United States Patent
Shin

(10) Patent No.: US 11,109,694 B2
(45) Date of Patent: Sep. 7, 2021

(54) SMART MAKEUP MIRROR DEVICE HAVING A DISPLAY AND INTEGRATING WITH AN ARTIFICIAL INTELLIGENCE VOICE ASSISTANT

(71) Applicant: ICON AI Inc., Seoul (KR)

(72) Inventor: Min Young Shin, Seoul (KR)

(73) Assignee: ICON AI Inc., Seoul (KR)

( * ) Notice: Subject to any disclaimer, the term of this patent is extended or adjusted under 35 U.S.C. 154(b) by 0 days.

(21) Appl. No.: 17/173,428

(22) Filed: Feb. 11, 2021

(65) Prior Publication Data

US 2021/0244204 A1 Aug. 12, 2021

(30) Foreign Application Priority Data

Feb. 11, 2020 (KR) .................. 10-2020-0016415

(51) Int. Cl.
*G02B 5/08* (2006.01)
*A47G 1/02* (2006.01)
(Continued)

(52) U.S. Cl.
CPC .................. *A47G 1/02* (2013.01); *A47G 1/24* (2013.01); *A61B 5/441* (2013.01); *A61N 5/0618* (2013.01);
(Continued)

(58) Field of Classification Search
CPC .... A47G 1/02; A47G 1/24; A47G 2001/1673; A47G 2200/146; A47G 2200/143;
(Continued)

(56) References Cited

U.S. PATENT DOCUMENTS

2008/0106705 A1* 5/2008 Cortenraad ............ G02B 30/25
353/98

FOREIGN PATENT DOCUMENTS

KR 200484824 Y1 10/2017
KR 20180037909 A 4/2018
(Continued)

OTHER PUBLICATIONS

Business Wire, "ICON.AI Named as CES 2020 Innovation Awards Winner With Its Venus, Smart Makeup Mirror With Alexa Builtin . . . Changing the Beauty Industry With Artificial Intelligence", Jan. 5, 2020 08:30 PM Eastern Standard Time, URL: https://www.businesswire.com/news/home/20200105005028/en/ICON.AI-Named-C.
(Continued)

*Primary Examiner* — Charlotte M Baker
(74) *Attorney, Agent, or Firm* — Maier & Maier, PLLC

(57) ABSTRACT

A smart makeup mirror device includes a main body, a display mirror unit rotatably mounted in the main body, and a speaker. The display mirror unit includes a display module, a makeup mirror, a support frame for fixing the makeup mirror, and a mood lamp mounted on a rear surface of the support frame. The support frame rotates with respect to the main body so that an angle with respect to the makeup mirror and the ground is changed, or rotate in a circumferential direction of the makeup mirror. The display module is oriented horizontally or vertically when the support frame is rotated in the circumferential direction of the makeup mirror. The mood lamp illuminates a mood light toward a floor surface when a rear surface of the display mirror unit is rotated at a specific angle with respect to the main body to face the floor surface.

13 Claims, 19 Drawing Sheets

(51) Int. Cl.
  *A61B 5/00* (2006.01)
  *A47G 1/24* (2006.01)
  *A61N 5/06* (2006.01)
  *G06F 3/16* (2006.01)
  *A47G 1/16* (2006.01)
(52) U.S. Cl.
  CPC ...... *G06F 3/167* (2013.01); *A47G 2001/1673* (2013.01); *A47G 2200/143* (2013.01); *A47G 2200/146* (2013.01); *A61N 2005/0651* (2013.01); *G06T 2207/30201* (2013.01)
(58) Field of Classification Search
  CPC ....... G06F 3/167; A61B 5/441; A61N 5/0618; A61N 2005/0651; G06T 2207/30201
  USPC ............................................. 359/838; 353/98
  See application file for complete search history.

(56) References Cited

FOREIGN PATENT DOCUMENTS

| KR | 101900450 B1 | 9/2018 |
| KR | 101912083 B1 | 10/2018 |
| KR | 102031512 B1 | 10/2019 |
| KR | 20190117434 A | 10/2019 |

OTHER PUBLICATIONS

Notice of Preliminary Rejection dated Jun. 29, 2020 in corresponding Korean application No. 10-2020-0016415; 9 pgs.
Notice of Allowance dated Nov. 29, 2020 in corresponding Korean application No. 10-2020-0016415; 6 pgs.

* cited by examiner

SMART MAKEUP MIRROR DEVICE HAVING A DISPLAY AND INTEGRATING WITH AN ARTIFICIAL INTELLIGENCE VOICE ASSISTANT

CROSS-REFERENCE TO RELATED APPLICATION

This application is based on and claims priority to Korean Patent Application No. 10-2020-0016415, filed on Feb. 11, 2020, the application of which is incorporated herein in its entirety by reference.

TECHNICAL FIELD

The present disclosure relates to a smart makeup mirror device having a display and integrating with an artificial intelligence voice assistant.

BACKGROUND

In general, consumers demand cosmetics that are optimal for their skin condition, but it is very difficult for cosmetics produced in order not to cause skin troubles to most people to be suitable for a specific consumer's preference or skin condition.

Even luxury cosmetics of high prices are not customized cosmetics suitable for each individual consumer's skin condition but only cosmetics of mass production, and they have failed in providing accurate functions suitable for each consumer's skin condition in spite of their overly high prices.

In this regard, conventionally, a skin condition of a customer is measured using a skin diagnosis device, and a customized cosmetic product whose raw ingredient ratio is appropriately adjusted based on the measured customer's skin condition information is produced and provided to the customer.

SUMMARY

In view of above, an embodiment of the present disclosure provides a smart makeup mirror device having a display integrating with an artificial intelligence voice assistant.

In addition, the embodiment of the present disclosure provides an all-in-one multifunctional smart makeup mirror, and provides a makeup mirror, an artificial intelligence voice assistant (artificial intelligence assistant platform) function, a mood lamp, and a speaker for music playback in one device.

In addition, the embodiment of the present disclosure provides a user with: a simple diagnosis of the user's skin condition through a smart device; and a function of recommending related cosmetics suitable for the skin condition to the user through an artificial intelligence algorithm.

In addition, the embodiment of the present disclosure increases a user's convenience by providing a device having various functions applied such as: providing information such as music playback, weather information, and news through an LCD display mounted on a mirror, by integrating with an artificial intelligence voice assistant (artificial intelligence assistant platform); playing music on smartphones by integrating with Bluetooth in normal times; and providing a function of mood lamp lighting by rotating the mirror unit 90 degrees.

In accordance with an aspect of the present disclosure, there is provided a smart makeup mirror device having a display and integrating with an artificial intelligence voice assistant, including: a main body; a display mirror unit rotatably mounted in the main body; and a speaker mounted in the main body to output a sound, wherein the display mirror unit includes: a display module that outputs an image by implementing a preset display mode based on a voice signal or a touch signal of a user; a makeup mirror in which a portion of the makeup mirror is configured to reflect a light and another portion of the makeup mirror is configured to transmit an image output from the display module; a support frame for fixing the makeup mirror; and a mood lamp mounted on a rear surface of the support frame, wherein the support frame includes: a hinge support part configured to rotate with respect to the main body about a virtual first rotation axis extending in a direction parallel to ground; and a frame part configured to rotate with respect to the hinge support part about a virtual second rotation axis perpendicular to a mirror surface of the makeup mirror and the virtual first rotation axis, wherein the support frame is configured to rotate with respect to the main body so that an angle with respect to the makeup mirror and the ground is changed, or rotate in a circumferential direction of the makeup mirror, and the display module is configured to be oriented horizontally or vertically when the support frame is rotated in the circumferential direction of the makeup mirror, and wherein the mood lamp is controlled to illuminate a mood light toward a floor surface when a rear surface of the display mirror unit is rotated at a specific angle with respect to the main body to face the floor surface.

The display mirror unit may further include: a camera disposed in the support frame to take a photograph of a skin condition of the user; and one or more microphones mounted in one end portion of the support frame to receive the voice signal of the user.

The display mirror unit may further include a ring light disposed in an edge of the support frame to provide LED lighting to the user.

The display mirror unit may further include: a recognition sensor that operates on and off modes of the ring light based on a detection of the user; and a light adjustment module that operates a brightness adjustment mode of the ring light when a touch-and-drag gesture is input from one end to another end by the user.

When the support frame is rotated at a predetermined angle in a circumferential direction of the support frame, the display module may be integrated with an artificial intelligence voice assistant by the voice signal of the user.

The display mode may include: an artificial intelligence voice assistant mode that provides life information based on a preset algorithm based on the voice signal or touch signal of the user; a skin diagnosis mode that diagnoses the skin condition of the user photographed by the camera; and an augmented reality makeup mode that provides information on a cosmetic product suitable for the skin condition of the user based on a skin diagnosis result obtained from the skin diagnosis mode.

The support frame may include a plurality of heat dissipating holes for discharging a heat generated from the display mirror unit to an outside.

The mood lamp may be provided in a form of line-LED which circumferentially and continuously extends around a center of the rear surface of the support frame.

The main body may include: a tower housing including: a lower circumferential surface in which a plurality of speaker grill holes are formed in a lower circumferential surface of the tower housing; and an upper end to which the display mirror unit is rotatably mounted; a control switch disposed on a front surface of the tower housing; and a charging port disposed on a rear surface of the tower housing to supply power.

The main body may further include a suction cup pad for fixing to the floor surface, wherein the suction cup pad is made of an elastic material and disposed on a bottom surface of the tower housing.

The control switch may include: an artificial intelligence voice assistant switch for turning on and off an integration with the artificial intelligence voice assistant controlling an operation of the display mirror unit based on the voice signal; a Bluetooth switch for turning on and off a Bluetooth function between a mobile phone of the user and the speaker; and a volume switch for adjusting a volume of the speaker.

When the artificial intelligence voice assistant switch is turned on and the display module rotates at a predetermined angle in the circumferential direction, the artificial intelligence voice assistant may be implemented by the voice signal of the user.

The artificial intelligence voice assistant mode may be implemented when the display module is horizontally oriented, and the skin diagnosis mode or the augmented reality makeup mode may be implemented when the display module is vertically oriented.

According to the embodiment of the present disclosure, a user's skin condition may be easily diagnosed, and a beauty product (cosmetics) suitable for the user's skin condition may be recommended and used conveniently according to the diagnosis result. In addition, by collecting customer data such as what cosmetics a user of the smart makeup mirror device of the present disclosure prefers to use every day and the user's area of interest, cosmetic manufacturers have advantages of being able to incorporate the data into product developments and use it as a means of advertising, promotion, and marketing, and communicate closely with customers through two-way communication through the present disclosure.

Further, according to the embodiment of the present disclosure, there is an advantage of being able to be provided with a variety of life information (weather, beauty contents, latest trends, etc.) as well as music desired by a user through the user's voice signal.

Further, according to the embodiment of the present disclosure, an all-in-one multifunctional smart makeup mirror may be provided. In other words, as a makeup mirror, artificial intelligence voice assistant (artificial intelligence assistant platform) function, a mood lamp, and a speaker for music playback are all provided in one device, there is an advantage of being able to utilize space efficiently and reduce purchasing costs because various functions may be used with one device without separately purchasing a product for each function.

Further, according to the embodiment of the present disclosure, there are advantages of being able to: provide LED lighting that helps skin care through a ring light provided on the front of a makeup mirror; and use a rear surface of the makeup mirror as a mood lamp when the rear surface of the makeup mirror is rotated toward the floor.

DETAILED DESCRIPTION OF THE EMBODIMENTS

Figure 1:
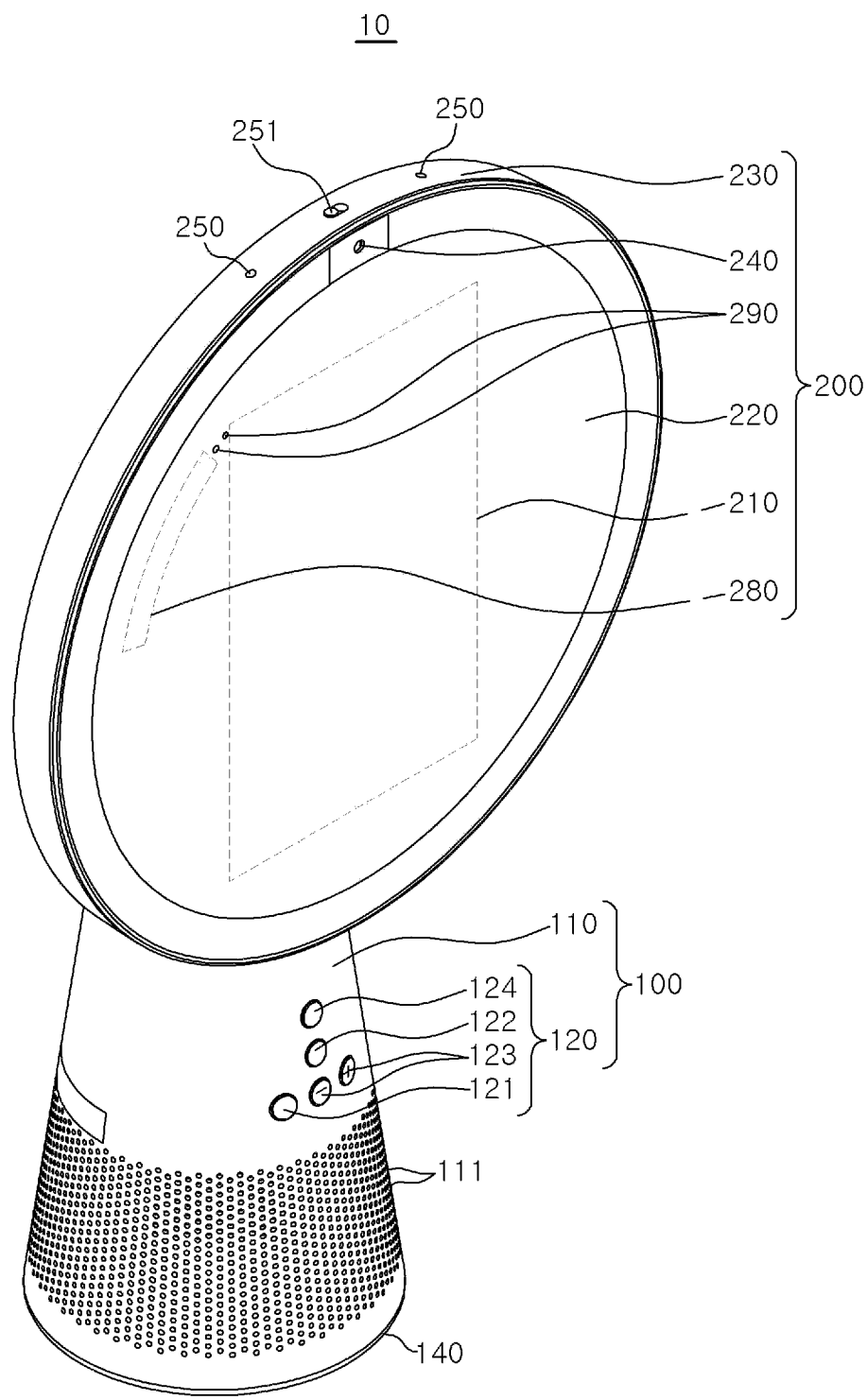
FIG. 1 is a perspective view illustrating a front side of a smart makeup mirror device having a display and integrating with an artificial intelligence voice assistant according to an embodiment of the present disclosure.
Figure 2:
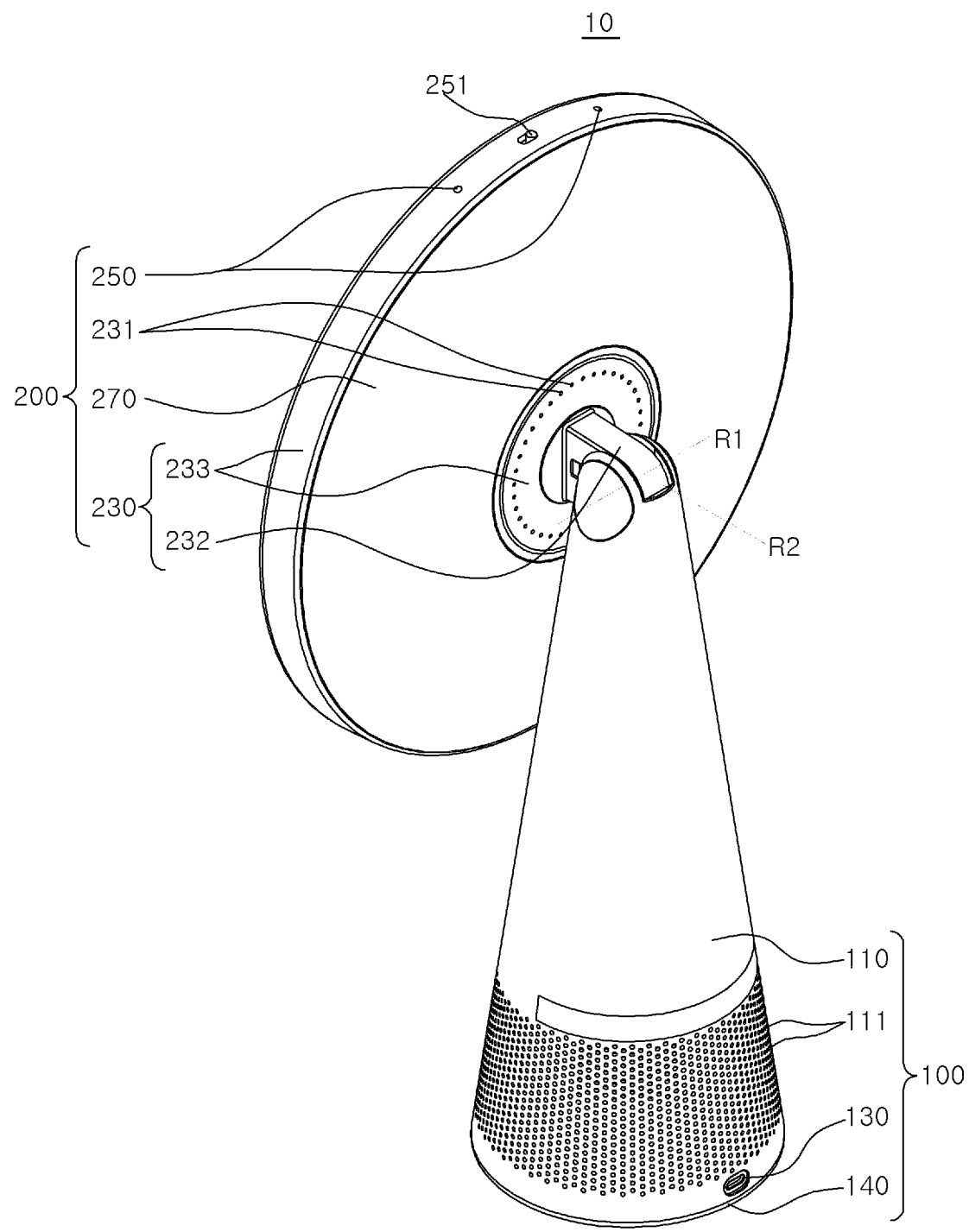
FIG. 2 is a side view illustrating a rear side of the smart makeup mirror device having the display and integrating with the artificial intelligence voice assistant according to the embodiment of the present disclosure.
Figure 3:
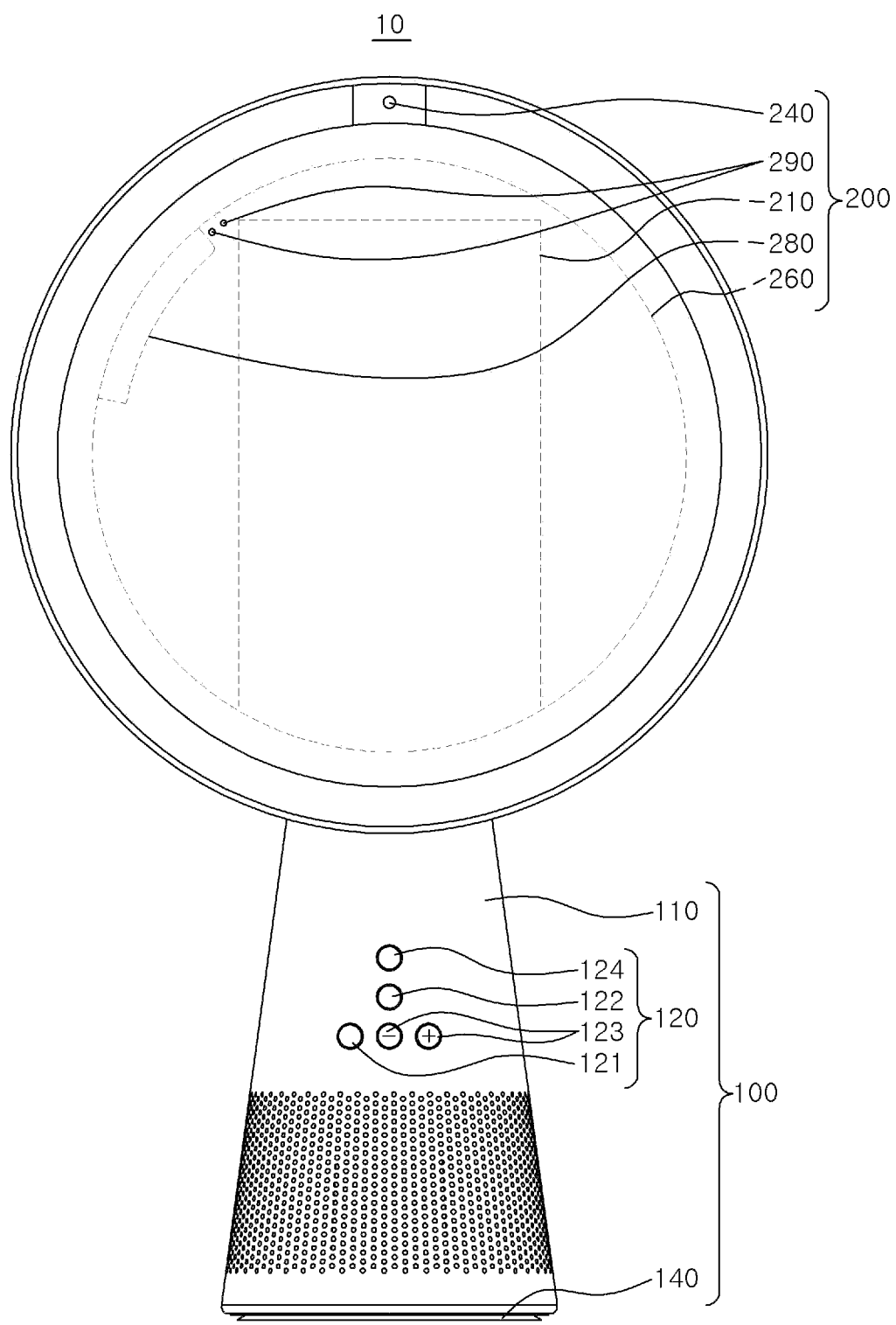
FIG. 3 is a front view illustrating the smart makeup mirror device having the display and integrating with the artificial intelligence voice assistant according to the embodiment of the present disclosure.

First of all, in adding reference numerals to elements of each drawing, it should be noted that the same elements are intended to have the same numerals as much as possible even if they are indicated in different drawings. In addition, in describing the present disclosure, when it is determined that a detailed description of a related known configuration or function may obscure the subject matter of the present disclosure, a detailed description thereof will be omitted.

Hereinafter, an embodiment of the present disclosure will be described in detail with reference to the accompanying drawings.

As shown in FIGS. 1 to 6, a smart makeup mirror device (hereinafter, referred to as a "smart device 10") having a display and integrating with an artificial intelligence voice assistant according to an embodiment of the present disclosure may include a main body 100, a display mirror unit 200, a speaker 300, a battery 400, and a controller 500.

Specifically, the main body 100 may rotatably support the display mirror unit 200. The main body 100 may have a conical tower shape. A speaker 300 may be equipped with a lower circumferential surface of the main body 100, and a battery 400 may be equipped therein.

The main body 100 may include a tower housing 110, a control switch 120, a charging port 130, and a suction cup pad 140.

The tower housing 110 of the main body 100 may have a conical tower shape to stably support the display mirror unit 200 while being easily gripped by a user. In this embodiment, the tower housing 110 is configured in the conical tower shape, but is not limited thereto, and the shape of the tower housing 110 may be variously changed.

A plurality of speaker grill holes 111 may be formed in a lower circumferential surface of the tower housing 110. Since the speaker grill holes 111 extend through the lower circumferential surface of the tower housing 110 in a circumferential direction thereof, sound output by the speaker 300 may be emitted in a radial direction of the tower housing 110.

The display mirror unit 200 may be rotatably mounted on an upper end of the tower housing 110. The display mirror unit 200 may be rotated with respect to the tower housing 110 about an axis extending parallel to the ground. In addition, the upper end of the tower housing 110 may be rotatably coupled to the display mirror unit 200 through a hinge.

The control switch 120 may be provided on a front of the tower housing 110 to control the operation of the display mirror unit 200. The smart device 10 may be manipulated to implement an artificial intelligence voice assistant (artificial intelligence assistant platform) function through the control switch 120. The control switch 120 may include a artificial intelligence voice assistant switch 121, a Bluetooth switch 122, a volume switch 123, and a sleep switch 124. The artificial intelligence voice assistant switch 121 may turn on and off a function integrated with the artificial intelligence voice assistant that controls the operation of the display mirror unit 200 through a voice signal input through a microphone 250. The Bluetooth switch 122 may turn on and off a Bluetooth function between a user's mobile phone and the speaker 300. The volume switch 123 may adjust the volume of the speaker 300 to increase or decrease. The sleep switch 124 may provide a function of temporarily turning off an LCD display of the display mirror unit 200.

Figure 4:
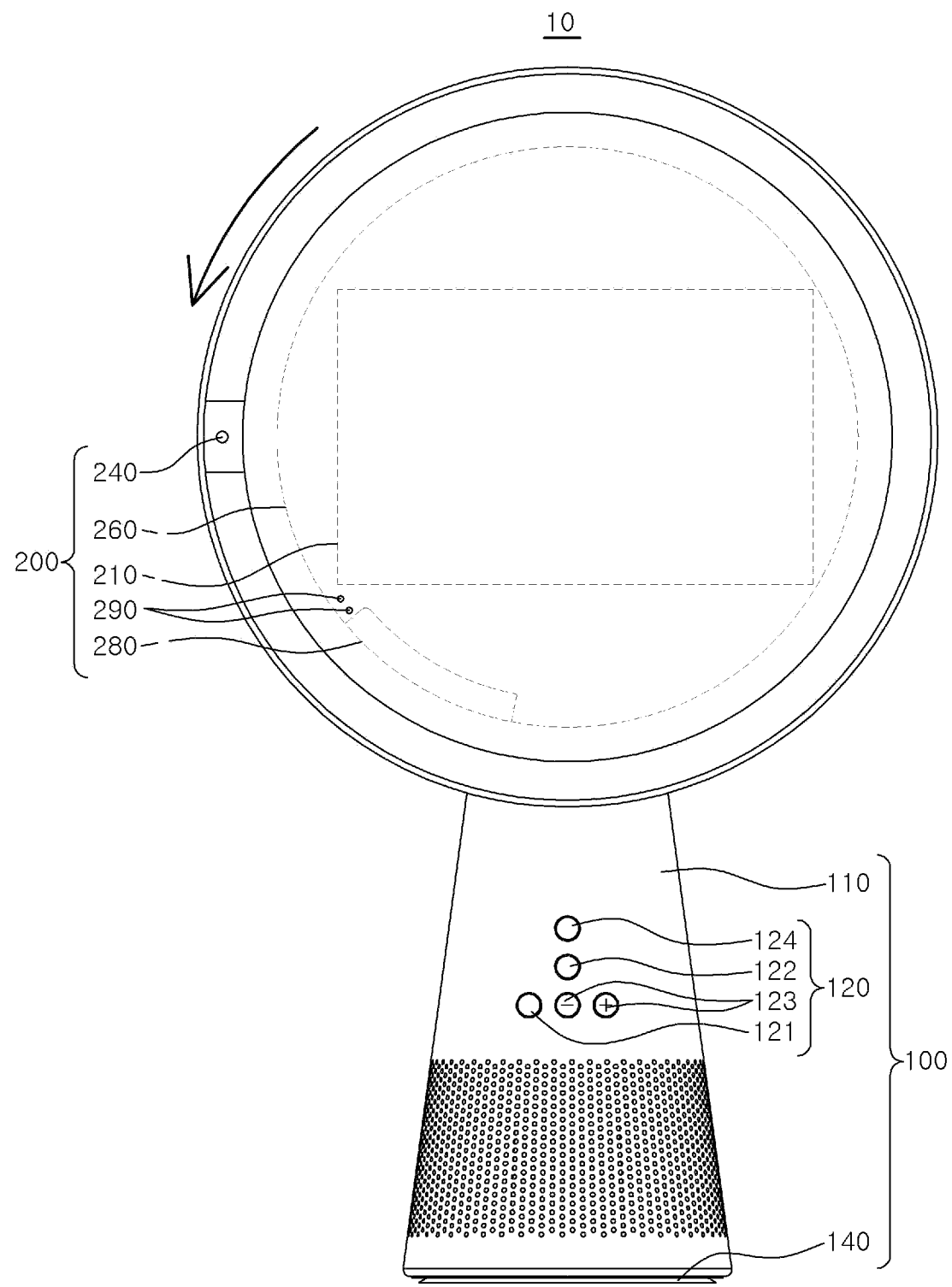
FIG. 4 is a front view illustrating the smart makeup mirror device having the display and integrating with the artificial intelligence voice assistant when a display mirror unit is rotated 90 degrees in the circumferential direction in FIG. 3.

For example, as shown in FIG. 4, once the artificial intelligence voice assistant switch 121 is turned on by a user, the artificial intelligence voice assistant function may be controlled to be implemented by the user's voice signal when the display module 210 rotates through a predetermined angle in the circumferential direction (for example, 90 degrees counterclockwise with respect to the front).

In this connection, the artificial intelligence voice assistant function may be implemented as an artificial intelligence voice assistant (artificial intelligence assistant platform) to which a voice recognition technology for converting a voice signal received through the microphone 250 into words or sentences is applied. Examples of such artificial intelligence voice assistants may be Amazon Alexa, Google Assistant, SK Telecom's NUGU, and Naver's Clova. The artificial intelligence voice assistant function processes the user's voice signal as an input signal, and can provide various artificial intelligence assistant services such as music playback, schedule management, alarm service reservation guidance function, speaker operation as well as searching through a preset algorithm. Since the artificial intelligence voice assistant function is a concept corresponding to an ordinary artificial intelligence voice assistant function, a detailed description thereof will be omitted.

In addition, the artificial intelligence voice assistant may control the operation of nearby electronic products using a network hub. For example, once a user feeds the smart device 10 with a voice signal for operating an electronic product (smart TV, smart air conditioner, smart light, smart security system, etc.), the artificial intelligence voice assistant may perform a remote control function in order for operation of the electronic product through an infrared signal generator (not shown).

The charging port 130 may be provided on a rear of the tower housing 110 to supply power to the display mirror unit 200, the speaker 300, the battery 400, etc. The charging port 130 may be electrically connected between the battery 400 built in the main body 100 and an external power source. Since the battery 400 is electrically connected to the display mirror unit 200, the display mirror unit 200 may be supplied with power through the battery 400.

The suction cup pad 140 may include an elastic material such as silicon, which is provided on a bottom of the tower housing 110. The suction cup pad 140 may fix the main body 100 to a top of a table by increasing the adhesion of a bottom surface of the main body 100 to the top of the table.

The display mirror unit 200 may include a display module 210, a makeup mirror 220, a support frame 230, a camera 240, a microphone 250, a ring light 260, a mood lamp 270, a recognition sensor 290 and a light adjustment module 280.

The display module 210 may include a smart terminal capable of outputting an image by implementing preset display modes (application, programming, etc.) according to a user's voice signal or touch signal.

In this regard, the display modes may include an artificial intelligence voice assistant mode, a skin diagnosis mode, and an augmented reality (AR) makeup mode. The artificial intelligence voice assistant mode may provide various information in accordance with a user's voice signal or touch signal based on a preset algorithm, for example, an algorithm that can be realized in an artificial intelligence voice assistant of an ordinary display module 210, or an algorithm that receives corresponding information from a server. The information received by such algorithms may be, e.g., life information such as weather, information on people, objects, etc., but the spirit of the present disclosure is not necessarily limited thereto. Since the artificial intelligence voice assistant applied to the display module 210 corresponds to the function of the artificial intelligence voice assistant that can be embodied in an ordinary smart terminal, a detailed description thereof will be omitted.

For example, in the artificial intelligence voice assistant mode, when a user's voice signal is received, weather information, beauty content information, the latest trend information, makeup information, hair and nail-related information, or the like may be provided through preset algorithms via a voice or a screen of the display module 210.

In the skin diagnosis mode, once a user's skin condition is photographed by the camera 240, the user's skin condition may be diagnosed using information on the photographed skin condition (pores, redness, wrinkles, skin texture, blemishes, etc.).

In the AR makeup mode, once a user's skin condition is diagnosed through the skin diagnosis mode, information on a cosmetic product (cosmetics, skin care, etc.) suitable for the user's skin condition is recommended based on the user's skin diagnosis result, and the user may receive and conveniently use the information. In addition, by collecting customer data such as what cosmetics a user of the smart device 10 of the present disclosure prefers to use every day and the user's area of interest, cosmetic manufacturers may incorporate the data into product developments and use it as a means of advertising, promotion, and marketing, and communicate closely with customers through two-way communication through the smart device 10 of the present disclosure.

Although the artificial intelligence voice assistant mode, the skin diagnosis mode, and the AR makeup mode as display modes of the display module 210 are described in this embodiment, the spirit of the present disclosure is not necessarily limited thereto, and the display module 210 may embody various other types of display modes.

The display module 210 may be selectively oriented horizontally or vertically by rotation. When the display module 210 is oriented in the horizontal direction, some of the plurality of display modes may be implemented, and when the display module 210 is oriented in the vertical direction, another part of the plurality of display modes may be implemented. The display module 210 may be provided in a rectangular shape.

For example, when the display module 210 is oriented in the horizontal direction, the artificial intelligence voice assistant mode may be implemented, and when the display module 210 is oriented in the vertical direction, the skin diagnosis mode or the AR makeup mode may be implemented. In this regard, the horizontal direction means a direction parallel to a mirror surface of the makeup mirror 220 and the ground while the display mirror unit 200 is rotated to be erect, and the vertical direction means a direction parallel to the mirror surface of the makeup mirror 220 and perpendicular to the horizontal direction.

The makeup mirror 220 may be a one-way mirror that reflects some light and is penetrated by the rest of the light. The makeup mirror 220 may provide a mirror function like a mirror with a special coating application according to the brightness of light, and may provide a glass function (light transmission function) capable of being seen through. One-way transmission recognition can be achieved when one side of the mirror is brightly lit and the other side is dark (light transmission function). Whether the makeup mirror 220 is in a mirror mode or a transmission mode may be controlled by a sleep switch 124 of the controller 500.

The support frame 230 may be coupled to the upper end of the main body 100 through a hinge coupled to the main body 100 so as to be rotatable with respect to the main body 100 in a front-rear direction. The support frame 230 may include a hinge support part 232 for supporting the hinge and a frame part 233 surrounding the hinge support part 232. In other words, the support frame 230 may rotate about a virtual axis (virtual first rotation axis R1) extending in a direction parallel to ground with respect to the main body 100.

In addition, the support frame 230 may be configured to be rotate in a circumferential direction thereof. In other words, the support frame 230 may rotate about a virtual axis (virtual second rotation axis R2) that extends in a direction perpendicular to the mirror surface of the makeup mirror 220 and perpendicular to the first rotation axis R1. In the support frame 230, the frame part 233 may be rotated about the hinge support part 232. The support frame 230 may be provided in a disk shape. As the support frame 230 is rotated in the circumferential direction thereof, the display module 210 may be oriented horizontally or vertically.

The support frame 230 may fix the makeup mirror 220 to be disposed in a front surface of the support frame 230, and the mood lamp 270 may be provided on a rear surface of the support frame 230. A plurality of heat dissipating holes 231 may be formed in the support frame 230. The plurality of heat dissipating holes 231 may provide a passage through which heat generated from the display mirror unit 200 may be discharged to the outside.

The camera 240 may be provided in an upper end portion of the support frame 230 so as to take a photograph of a user's skin condition. A lens of the camera 240 may be opened or closed by a shutter 251. An image signal captured by the camera 240 may be provided to the display module 210.

With mounted on one end portion of the support frame 230, microphones 250 may receive a user's voice signal. For example, the microphones 250 may be provided in a pair that are spaced apart from each other on the upper end portion of the support frame 230. Of course, in addition to one pair of the microphones 250, the microphones 250 may be provided in four or six which form pairs.

With disposed in the upper end portion of the support frame 230, the microphones 250 may recognize a user's voice signal more effectively. Of course, the present disclosure is not limited thereto, and the microphones 250 may be positioned on a side end portion of the support frame 230. The voice signal received through the microphones 250 may be provided to the display module 210.

The ring light 260 may be provided in a ring shape along an edge of the support frame 230. The ring light 260 may provide LED lighting toward a user.

Figure 5:
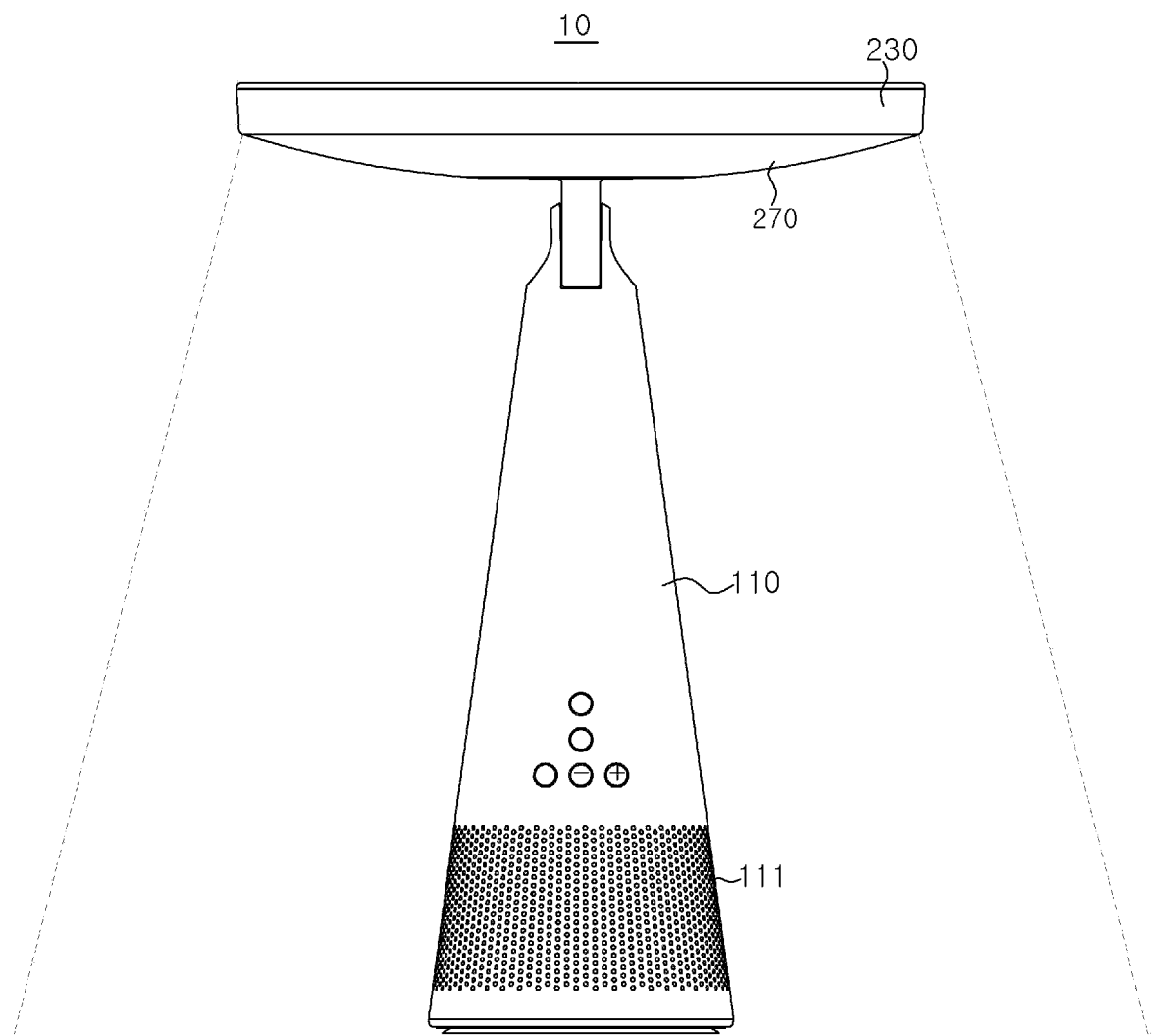
FIG. 5 is a front view illustrating a state in which a mood lamp of the smart makeup mirror device having the display and integrating with the artificial intelligence voice assistant is operated according to the embodiment of the present disclosure.

As shown in FIG. 5, the mood lamp 270 may be mounted on the rear surface of the support frame 230. The mood lamp 270 may be provided in the form of line-LED which circumferentially and continuously extend around a center of the rear surface of the support frame 230. When the display mirror unit 200 is rotated at a specific angle such as 90 degrees or 70 to 90 degrees with respect to the main body 100 (using a gyro sensor) so that the rear surface of the display mirror unit 200 faces a floor surface, the mood lamp 270 may be controlled to illuminate a mood light toward the floor.

The recognition sensor 290 may operate on and off modes of the ring light 260 based on the detection of a user. For example, when a user is positioned within a predetermined distance in front of the makeup mirror 220, the recognition sensor 290 may detect the user and operate the ring light 260 into the on mode. Further, when a user is not positioned within a predetermined distance in front of the makeup mirror 220, the recognition sensor 290 may not detect the user and may operate the ring light 260 into the off mode.

The light adjustment module 280 may operate a brightness adjustment mode of the ring light 260 when a touch-and-drag gesture is input from one end to another end by a user. The light adjustment module 280 may include a touch screen disposed in the rear surface of the makeup mirror 220. For example, when a touch-and-drag gesture is input from one end to another end by a user, the light adjustment module 280 may adjust the brightness of the ring light 260 to be gradually brighter. In addition, when a touch-and-drag gesture is input from one end to another end by a user, the light adjustment module 280 may adjust the brightness of the ring light 260 to be gradually darker.

In addition, the light adjustment module 280 may operate a color adjustment mode of the ring light 260 when a touching by a user is maintained for a predetermined time (for example, 2 seconds). For example, when a user touches at least a portion of the light adjustment module 280 once for a predetermined time, the color of the ring light 260 may change to a first color mode (natural color), and when the user touches at least a portion of the light adjustment module 280 once again for a predetermined time, the color of the ring light 260 may change to a second color mode (bright color), and when the user touches at least a portion of the light adjustment module 280 once again for a predetermined time, the color of the ring light 260 may change to a third color mode (warm color).

The speaker 300 may output a voice signal of the artificial intelligence voice assistant. For example, the speaker 300 may be controlled by the artificial intelligence voice assistant of the display module 210. The speaker 300 may be built into the main body 100 to output sound in the radial direction of the main body 100.

The battery 400 may be a rechargeable battery, and may receive power from the outside through the charging port 130. In addition, the battery 400 may supply charged power to the display mirror unit 200, the speaker 300, and the like.

Figure 6:
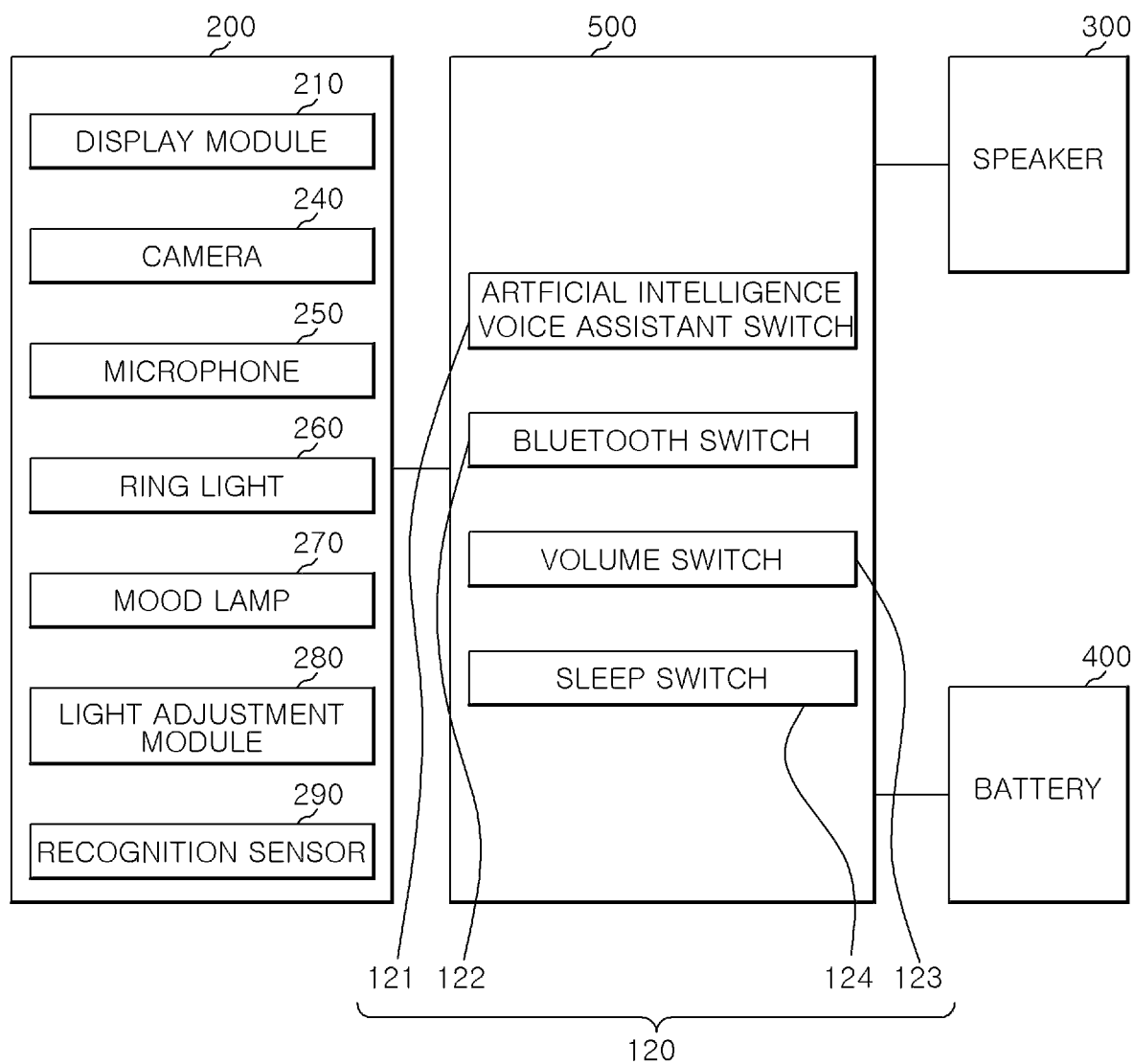
FIG. 6 is a block diagram illustrating a control flow of the smart makeup mirror device having the display and integrating with the artificial intelligence voice assistant according to the embodiment of the present disclosure.

As shown in FIG. 6, the controller 500 may include a PCB module to entirely control the display mirror unit 200, the speaker 300, and the battery 400. The controller 500 may be implemented by a computing device including a microphone processor, a memory, a communication module, and the like, and the implementation method thereof is obvious to those skilled in the art, and thus a detailed description thereof will be omitted.

Meanwhile, the smart device 10 according to the embodiment of the present disclosure may be operated in conjunction with an application provided to a communication terminal such as a smart phone. For example, in the smart device 10, the color and brightness of the ring light 260 and the mood lamp 270 may be respectively adjusted and the volume of the speaker 300 may be adjusted through the application provided to the communication terminal.

As described above, according to the embodiment of the present disclosure, after taking a selfie while looking at the camera 240 in the front, a user may easily have the user's skin condition be diagnosed through the skin diagnosis mode and the AR makeup mode among the display modes. The user may also receive recommendations on beauty products (cosmetics) suitable for the diagnosed skin condition. In addition, in order to implement the skin diagnosis mode and the AR makeup mode among the display modes through the smart device 10, or to take a selfie while looking at the camera 240 in the front, a user may rotate the display mirror unit 200 in one direction so that the display module 210 is oriented in the vertical direction. Further, through the smart device 10, in order to implement the artificial intelligence voice assistant mode among the display modes, the user may rotate the display mirror unit 200 in another direction so that the display module 210 is oriented in the horizontal direction.

In the artificial intelligence voice assistant mode, a user may be provided with a variety of life information (weather, beauty content, latest trends, etc.) as well as music desired by the user through the user's voice signal. In addition, the user may be provided with LED lighting that helps skin care through the ring light 260 provided in the front surface of the makeup mirror 220, and when the rear of the makeup mirror 220 is rotated toward the floor surface, the rear surface of the makeup mirror 220 may be used as a mood lamp 260.

Hereinafter, a smart makeup mirror device having a display and integrating with an artificial intelligence voice assistant according to a first modified example of the embodiment of the present disclosure will be described with reference to FIGS. 7 to 9.

Figure 7:
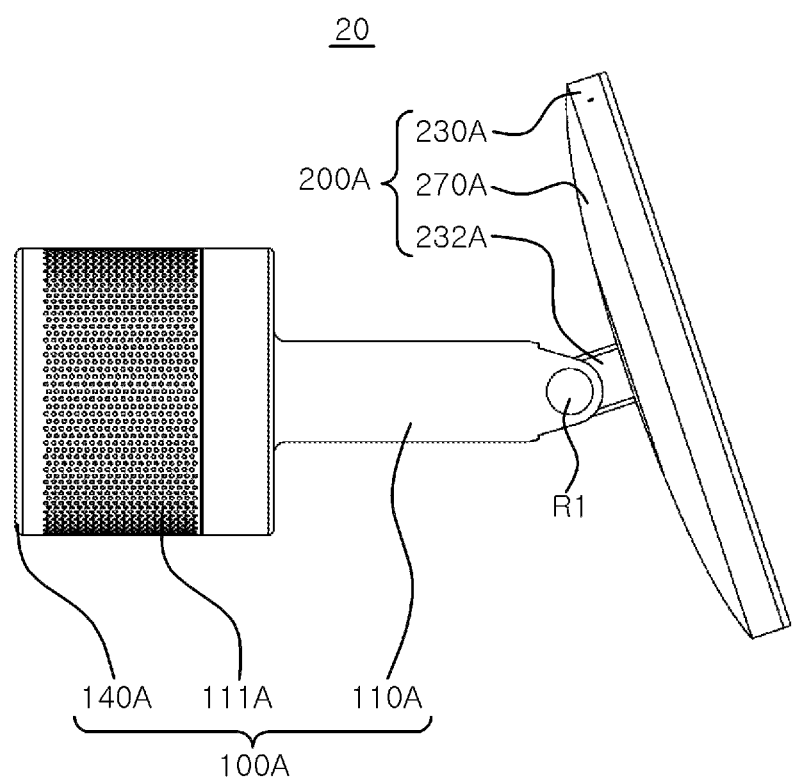
FIG. 7 is a side view illustrating a smart makeup mirror device having a display and integrating with an artificial intelligence voice assistant according to a first modified example of the embodiment of the present disclosure.
Figure 8:
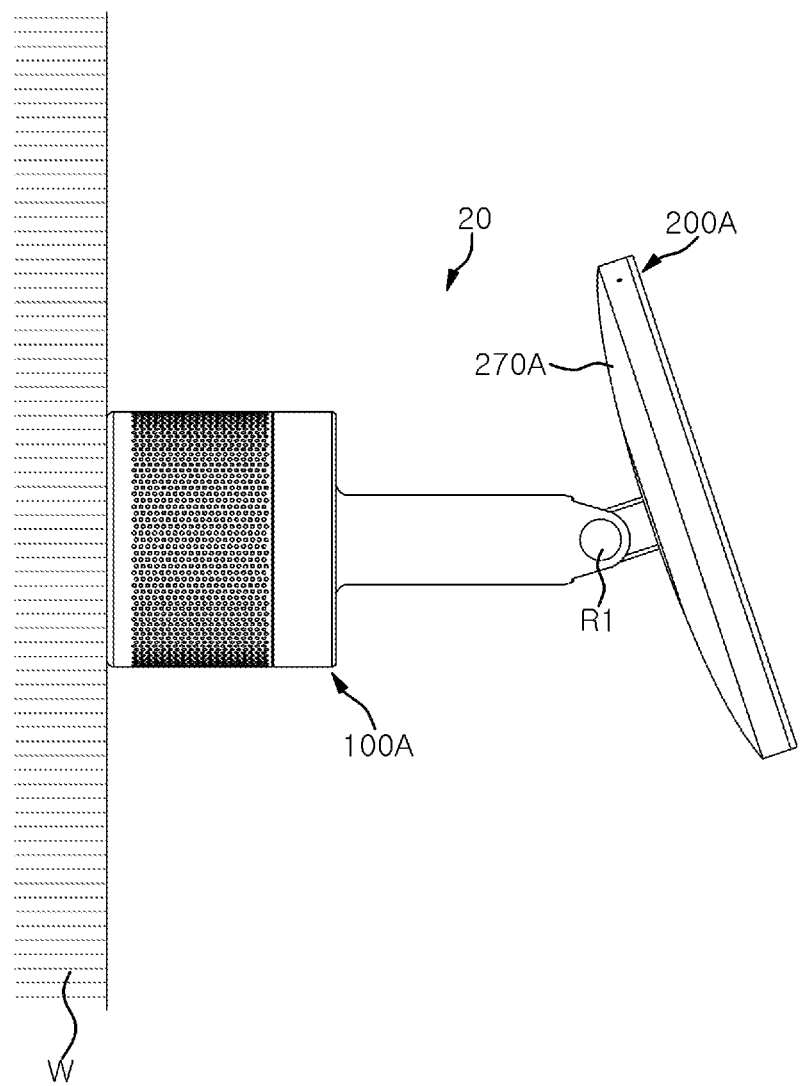
FIG. 8 is a side view illustrating a state in which the smart makeup mirror device having the display and integrating with the artificial intelligence voice assistant according to the first modified example of the present disclosure is mounted on a wall surface.
Figure 9:
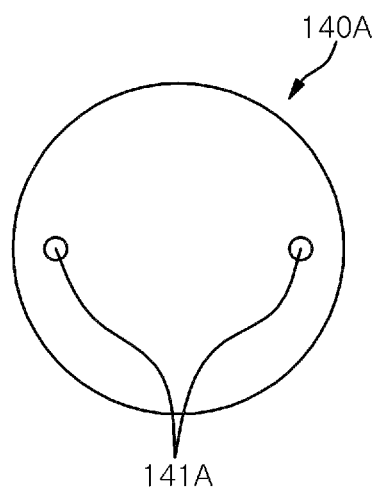
FIG. 9 shows a bottom surface of the smart makeup mirror device having the display and integrating with the artificial intelligence voice assistant according to the first modified example of the present disclosure

As shown in FIGS. 7 to 9, a smart makeup mirror device (hereinafter, referred to as a "smart device 20") having a display and integrating with an artificial intelligence voice assistant according to a first modified example of the embodiment of the present disclosure has the same configuration as the smart device 10 according to the embodiment of the present disclosure except that the smart device 20 is configured to be detachable to the wall surface.

Hereinafter, the smart device 20 will be mainly described on a configuration different from that of the smart device 10, and the description of the same configuration as the smart device 10 will be omitted.

The smart device 20 may include a display mirror unit 200A and a main body 100A.

The main body 100A may include a tower housing 110A. A mounting portion 140A is provided at one end in a longitudinal direction of the tower housing 110A, and a display mirror unit 200A is rotatably coupled at the other end in the longitudinal direction of the tower housing 110A through a hinge. Further, a plurality of speaker grill holes 111A may be formed in a portion of an outer surface of the tower housing 110A. Sound generated by a speaker built in the main body 100A may be output through the speaker grill holes 111A.

The mounting portion 140A may be provided on the main body 100A so that the smart device 20 is detachably mounted on a wall surface W. As shown in FIG. 9, one or more fastening holes 141A may be formed on a bottom surface of the mounting portion 140A. The fastening holes 141A may be coupled to a fastening protrusion such as a hook or a nail installed on the wall surface W. While FIG. 9 shows two fastening holes 141A spaced apart in a left and right direction, the location and number of the fastening holes 141A are not limited thereto, and may be appropriately changed as necessary.

The display mirror unit 200A may include a support frame 230A and a hinge support part 232A protruding and extending from the support frame 230A. The display mirror unit 200 may be rotated with respect to the tower housing 110A about an axis R1 extending parallel to the ground.

The display mirror unit 200A may further include a mood lamp 270A on a rear surface thereof. The mood lamp 270A may be provided in the form of line-LED which circumferentially and continuously extend around a center of the rear surface of the display mirror unit 200A. When the smart device 20 is mounted on the wall surface W, the mood lamp 270A may be controlled to irradiate mood lighting on the wall surface W.

As described above, the smart device 20 according to the first modified example of the embodiment of the present disclosure is configured to be mounted on a wall surface W. Therefore, a user can use the smart device 20 with mounted on the wall surface near a bathroom, a dressing table, or the like.

In addition, the smart device 20 according to the first modified example of the present disclosure can provide an all-in-one multifunctional smart makeup mirror, like the smart device 10. In other words, as a makeup mirror, artificial intelligence voice assistant (artificial intelligence assistant platform) function, a mood lamp, and a speaker for music playback are all provided in one device, there is an advantage of being able to utilize space efficiently and reduce purchasing costs because various functions may be used with one device without separately purchasing a product for each function.

Further, the smart device 20 according to the first modified example of the present disclosure can provide LED lighting that helps skin care through a ring light provided on the front of the display mirror unit, and use the mood lamp provided on the rear surface of the display mirror unit to irradiate a mood lighting on a wall surface.

Hereinafter, a smart makeup mirror device having a display and integrating with an artificial intelligence voice assistant according to a second modified example of the embodiment of the present disclosure will be described with reference to FIGS. 10 to 19.

A smart makeup mirror device 30 (hereinafter, referred to as a "smart device 30") having a display and integrating with an artificial intelligence voice assistant according to a second modified example of the embodiment of the present disclosure has the same configuration as the smart device 10 according to the embodiment of the present disclosure except that a display mirror unit is detachably mounted in a main body and a mood lamp is not provided.

Hereinafter, the smart device 30 will be mainly described on a configuration different from that of the smart device 10, and the description of the same configuration as the smart device 10 will be omitted.

The smart device 30 may include a display mirror unit 200B having a leg 234 and a main body 100B.

Figure 19:
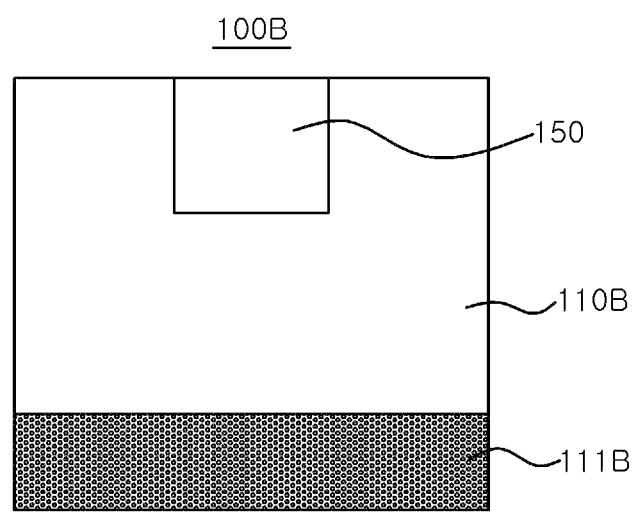
FIG. 19 is a front view of the main body which is separated from the display mirror unit in the smart makeup mirror device having the display and integrating with the artificial intelligence voice assistant according to the second modified example of the present disclosure.

The main body 100B may include a tower housing 110B. A plurality of speaker grill holes 111B may be formed in a lower portion of the tower housing 110B, and the display mirror unit 200B may be detachably mounted on an upper portion of the tower housing 110B. Sound generated by a speaker built in the main body 100A may be output through the speaker grill holes 111B. Further, as shown in FIG. 19, an insertion groove 150 may be provided in the upper portion of the tower housing 110B to extend inside the tower housing 110B.

The leg 234 of the display mirror unit 200B may be inserted into the insertion groove 150. The insertion groove 150 may extend obliquely from a front of the main body 100B toward an inside thereof, and a width of the insertion groove 150 may correspond to a width of the leg 234 of the display mirror unit 200B. In addition, one or more locking grooves (not shown) may be provided in the insertion groove 150 and a locking protrusion (not shown) may be provided in the leg 234. When the leg 234 of the display mirror unit 200B is inserted into the insertion groove 150, an insertion length of the leg may be adjusted using the locking protrusion and the locking groove. Alternately, each of the leg 234 and the insertion groove 150 may include a magnetic portion so that the insertion length of the leg may be adjusted by the magnetic force between the magnetic portions of the leg 234 and the insertion groove 150.

Figure 10:
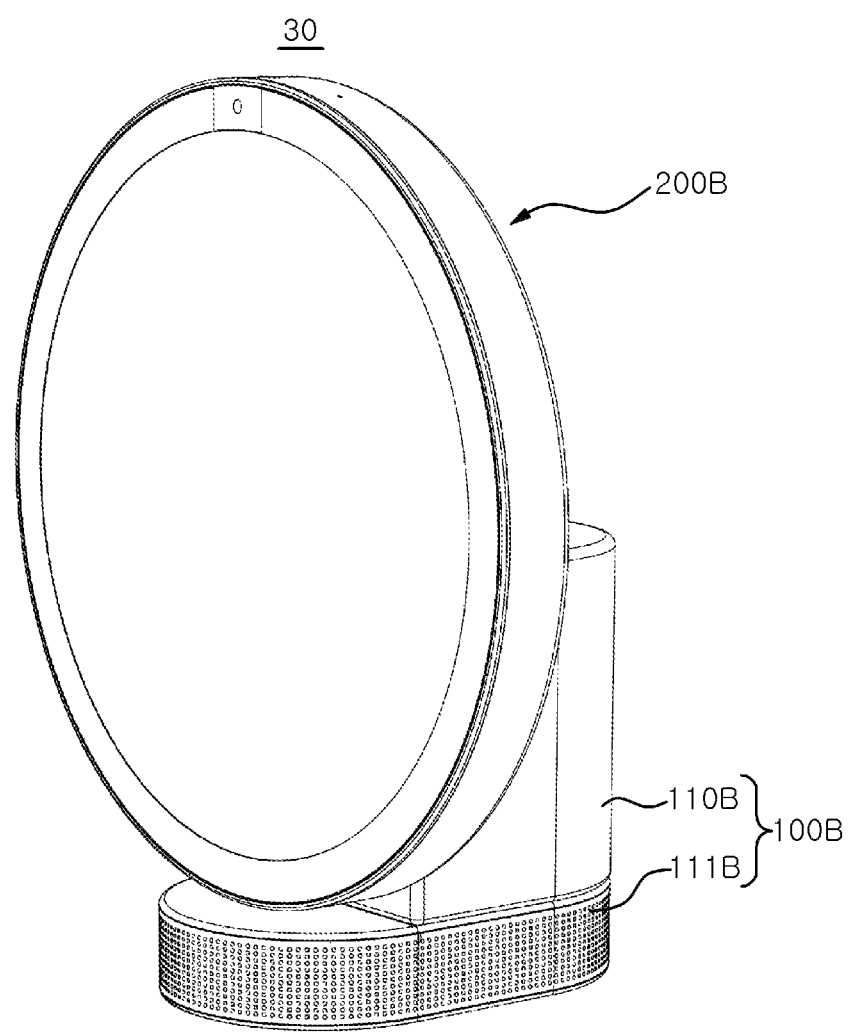
FIG. 10 is a perspective view illustrating a smart makeup mirror device having a display and integrating with an artificial intelligence voice assistant according to a second modified example of the embodiment of the present disclosure.
Figure 11:
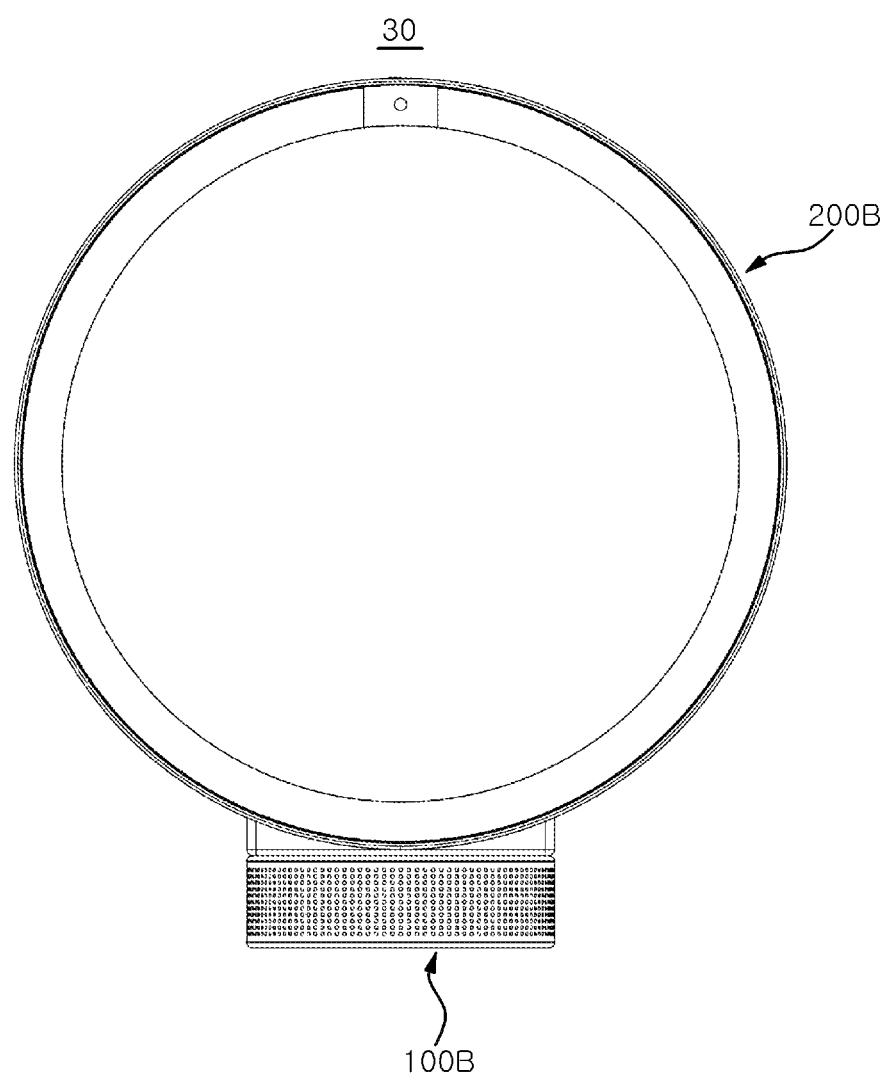
FIG. 11 is a front view of illustrating the smart makeup mirror device having the display and integrating with the artificial intelligence voice assistant according to the second modified example of the present disclosure.
Figure 12:
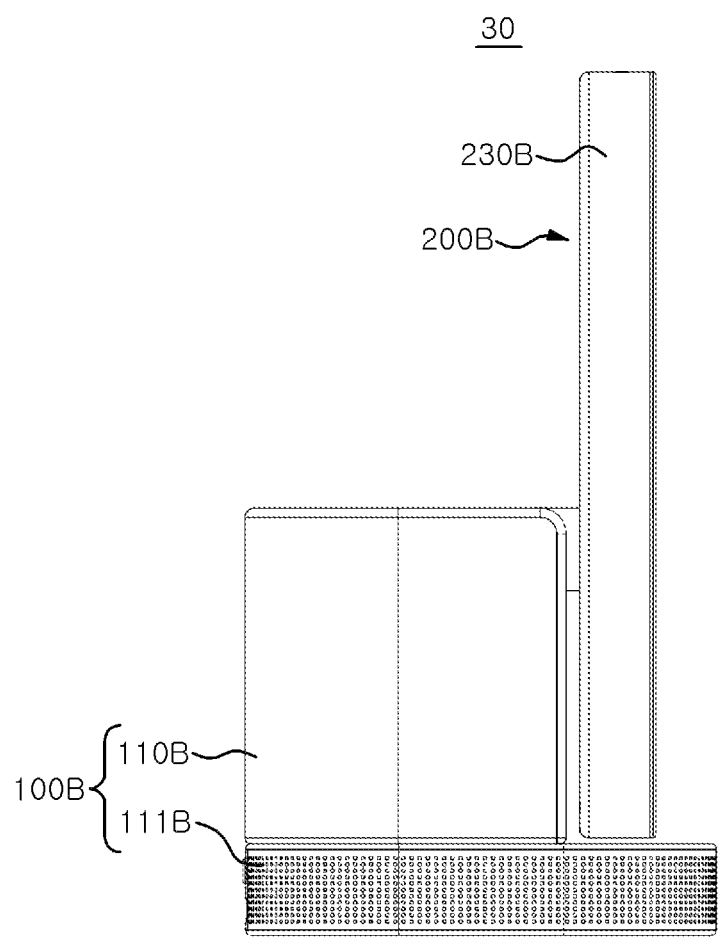
FIG. 12 is a side view of illustrating the smart makeup mirror device having the display and integrating with the artificial intelligence voice assistant according to the second modified example of the present disclosure.
Figure 13:
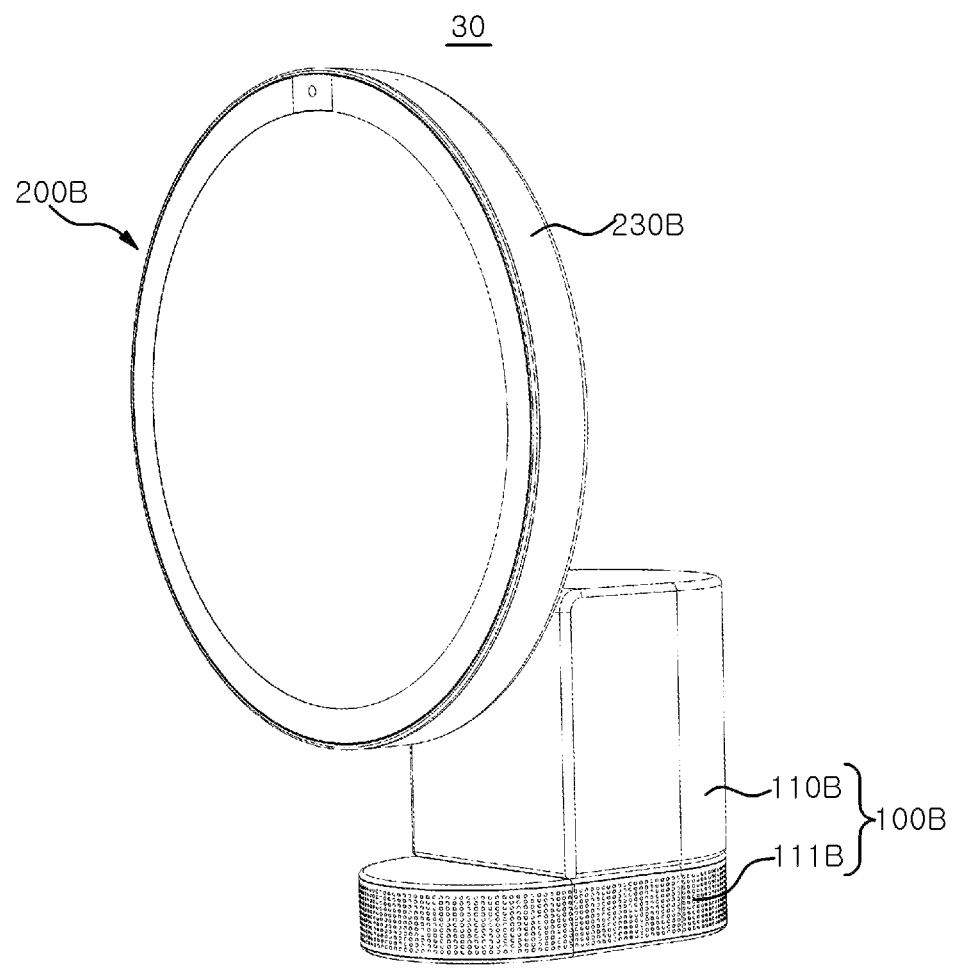
FIG. 13 is a perspective view showing a state in which a display mirror unit is upwardly raised from a main body in the smart makeup mirror device having the display and integrating with the artificial intelligence voice assistant according to the second modified example of the present disclosure.
Figure 14:
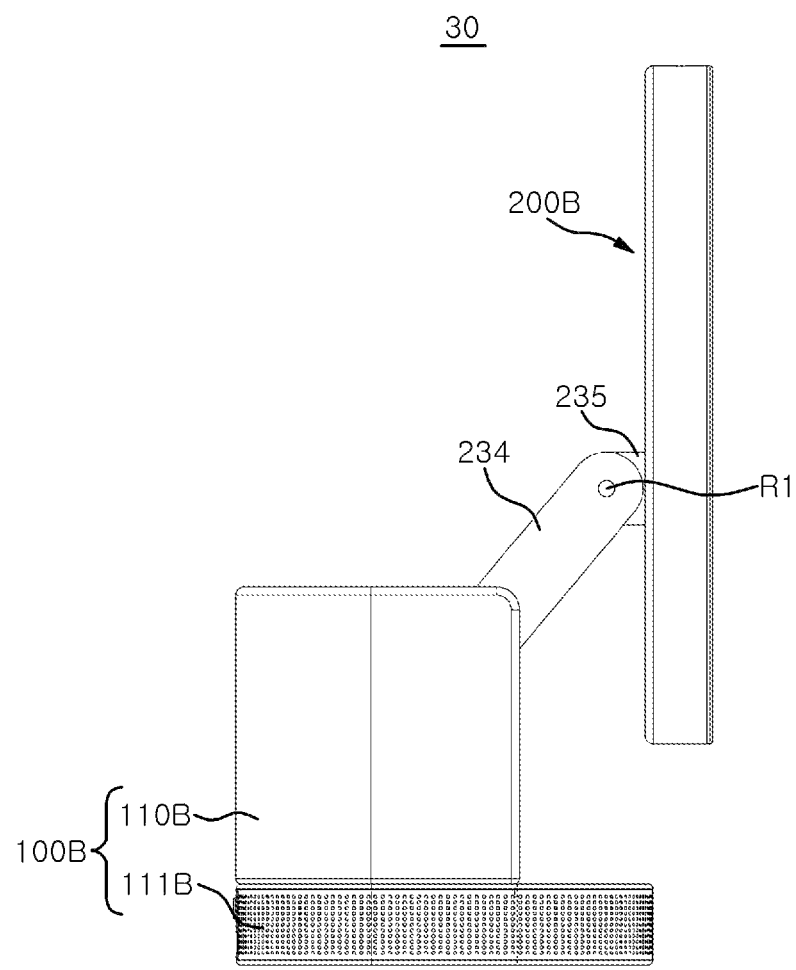
FIG. 14 is a side view showing the state in which the display mirror unit is upwardly raised from the main body in the smart makeup mirror device having the display and integrating with the artificial intelligence voice assistant according to the second modified example of the present disclosure.
Figure 15:
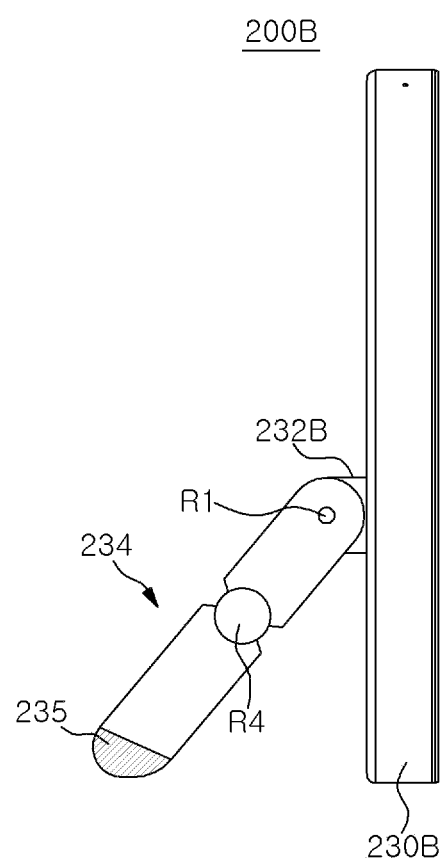
FIG. 15 shows a state in which the display mirror unit is separated from the main body in the smart makeup mirror device having the display and integrating with the artificial intelligence voice assistant according to the second modified example of the present disclosure.
Figure 16:
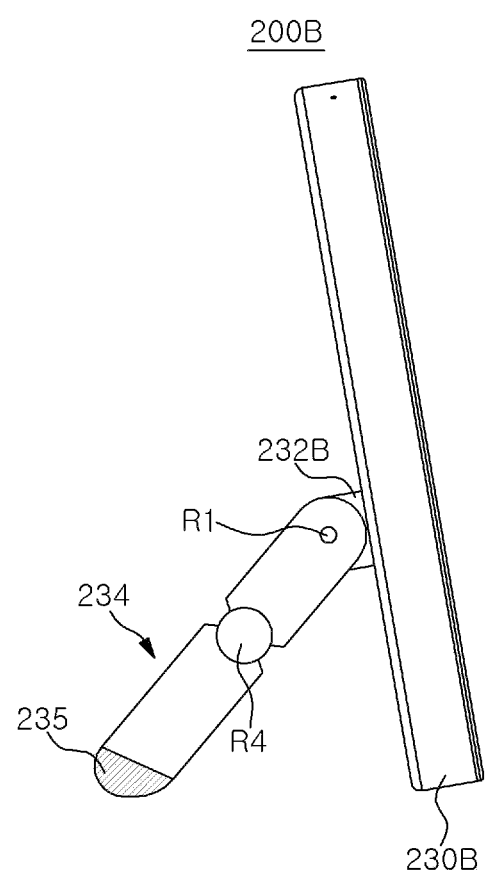
FIG. 16 illustrates a state in which an angle between a leg and a support frame in the display mirror unit shown in FIG. 15 is changed.
Figure 17:
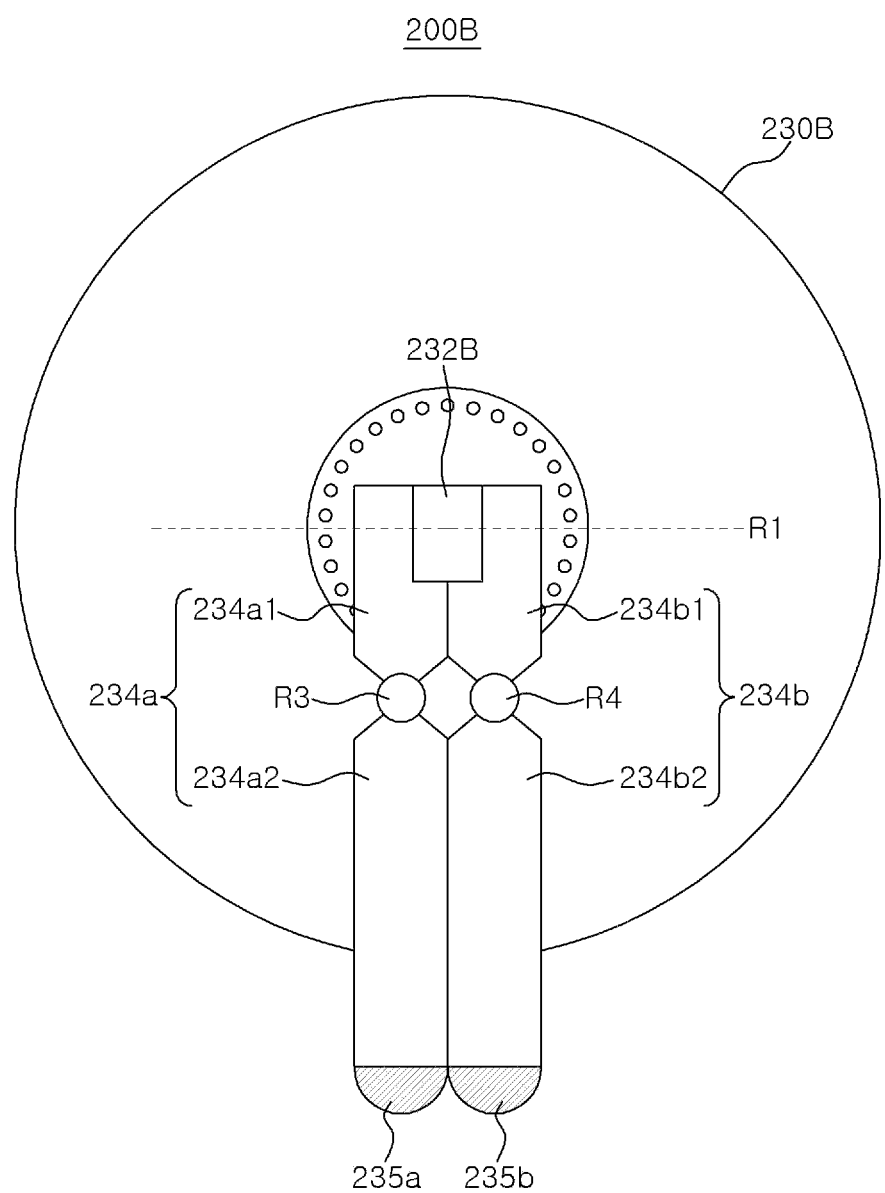
FIG. 17 is a rear view of the display mirror unit separated from the main body in the smart makeup mirror device having the display and integrating with the artificial intelligence voice assistant according to the second modified example of the present disclosure.
Figure 18:
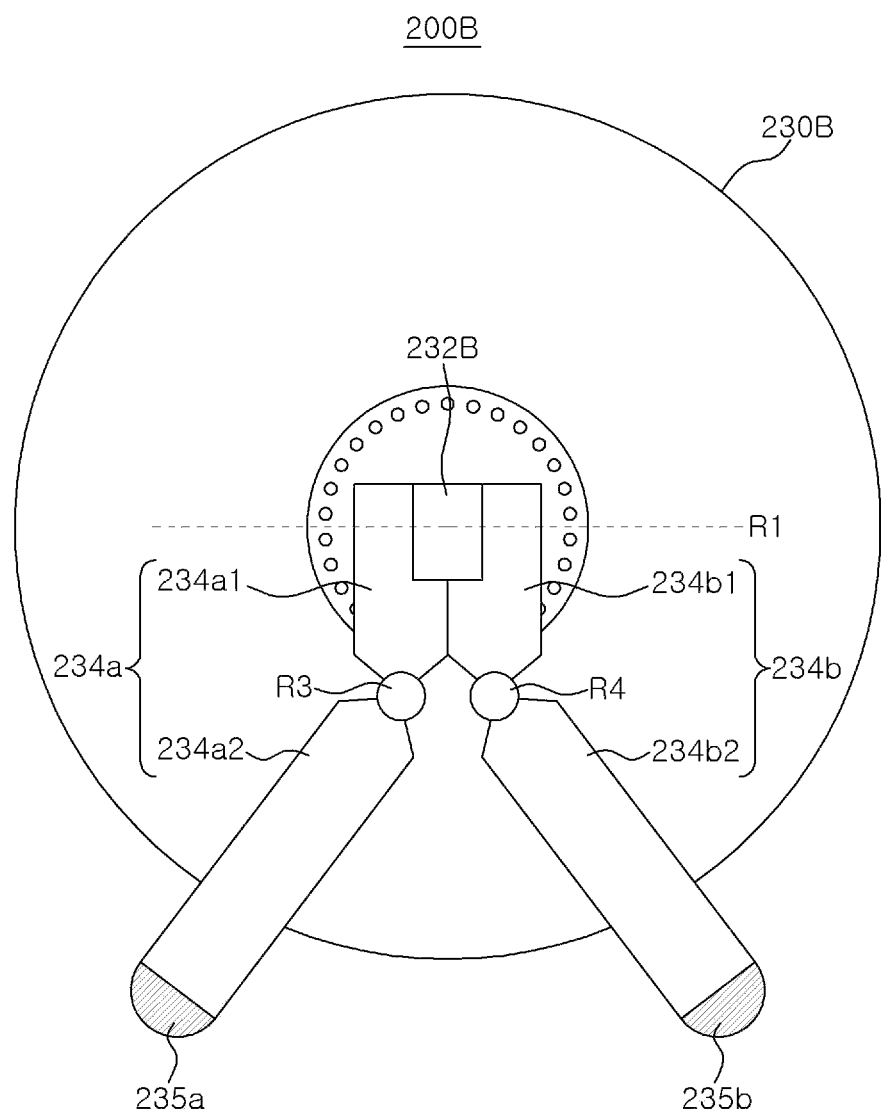
FIG. 18 is another rear view of the display mirror unit separated from the main body in the smart makeup mirror device having the display and integrating with the artificial intelligence voice assistant according to the second modified example of the present disclosure.

When the leg 234 is fully inserted into the insertion groove 150, the smart device 30 may maintain a contracted state as shown in FIGS. 10 to 12. In addition, when the leg 234 is incompletely inserted into and fixed in the insertion groove 150, a part of the leg 234 is exposed to an outside and the display mirror unit 200B is upwardly raised from the main body 100B as shown in FIGS. 13 and 14. Furthermore, when the leg 234 is separated from the insertion groove 150, the display mirror unit 200B may be used independently of the main body 100B.

As shown in FIGS. 15 to 18, the display mirror unit 200B may include a support frame 230B and a hinge support portion 232B extending to be protruded from the support frame 230B. In addition, the display mirror unit 200B may include a leg 234 which is rotatably connected to the hinge support portion 232B about an axis R1 provided in the hinge support portion 232B.

Further, the leg 234 may include a first leg 234a and a second leg 234b. The first leg 234a and the second leg 234b may be symmetrically extended from the hinge support portion 232B.

The first leg 234a may include a first rotation part 234a1 and a second rotation part 234a2. The first rotation part 234a1 is rotatably connected to the hinge support portion 232B about the axis R1. The second rotation part 234a2 is rotatably connected to the first rotation part 234a1 through an axis R3. The direction of the axis R3 is perpendicular to the direction of the axis R1. The first rotation part 234a1 may rotate about the axis R1. The second rotation part 234a2 may rotate about the axis R3.

Further, the second leg 234b may include a third rotation part 234b1 and a fourth rotation part 234b2. The third rotation part 234b1 is rotatably connected to the hinge support portion 232B about the axis R1. The fourth rotation part 234b2 is rotatably connected to the third rotation part 234b1 through an axis R4. The direction of the axis R4 may be perpendicular to that of the axis R1 and parallel to that of the axis R3. The third rotation part 234b1 may rotate about the axis R1. The fourth rotation part 234b2 may rotate about the axis R4.

When the display mirror unit 200B is separated from the main body 100B, a user can dispose the display mirror unit 200B on, e.g., a table at an angle desired by the user by adjusting an angle between the support frame 230B and the leg 234 by rotating the leg about the axis R1. Further, it is possible to stably support the display mirror unit 200B on the table or the like by adjusting a distance between the second rotation part 234a2 and the fourth rotation part 234b2.

Further, a non-slip pad 235 for preventing the slipping of the display mirror unit 200B may be disposed on a bottom surface of the leg 234. The non-slip pad 235 may include a first non-slip pad 235a attached on a bottom surface of the first leg 234a and a second non-slip pad 235b attached on a bottom surface of the second leg 234b.

As described above, in the smart device 30 according to the second modified example of the embodiment of the present disclosure, the display mirror unit 200B can be attached to or detached from the main body 100B.

With such configuration, the main body 100B and the display mirror unit 200B can be used as one body, and also the display mirror unit 200B can be separated from the main body 100B so that the display mirror unit 200B may be independently used of the main body 100B.

While the disclosure has been shown and described with respect to the preferred embodiments, the present disclosure is not limited to specific embodiments, and should be interpreted by following claims. Further, it will be understood by those skilled in the art that various changes and modifications may be made without departing from the scope of the disclosure.

What is claimed is:

1. A smart makeup mirror device having a display and integrating with an artificial intelligence voice assistant, comprising:
   a main body;
   a display mirror unit rotatably mounted in the main body; and
   a speaker mounted in the main body to output a sound, wherein the display mirror unit includes:
   a display module that outputs an image by implementing a preset display mode based on a voice signal or a touch signal of a user;
   a makeup mirror in which a portion of the makeup mirror is configured to reflect a light and another portion of the makeup mirror is configured to transmit an image output from the display module;
   a support frame for fixing the makeup mirror; and
   a mood lamp mounted on a rear surface of the support frame,
   wherein the support frame includes:
   a hinge support part configured to rotate with respect to the main body about a virtual first rotation axis extending in a direction parallel to ground; and
   a frame part configured to rotate with respect to the hinge support part about a virtual second rotation axis perpendicular to a mirror surface of the makeup mirror and the virtual first rotation axis,
   wherein the support frame is configured to rotate with respect to the main body so that an angle with respect to the makeup mirror and the ground is changed, or rotate in a circumferential direction of the makeup mirror, and
   the display module is configured to be oriented horizontally or vertically when the support frame is rotated in the circumferential direction of the makeup mirror, and
   wherein the mood lamp is controlled to illuminate a mood light toward a floor surface when a rear surface of the display mirror unit is rotated at a specific angle with respect to the main body to face the floor surface.

2. The smart makeup mirror device of claim 1, wherein the display mirror unit comprises:
   a support frame rotatably connected to the main body, the makeup mirror being mounted on a front surface of the support frame;
   a camera disposed in the support frame to take a photograph of a skin condition of the user; and
   one or more microphones mounted in one end portion of the support frame to receive the voice signal of the user.

3. The smart makeup mirror device of claim 2, wherein the display mirror unit further comprises a ring light disposed in an edge of the support frame to provide LED lighting to the user.

4. The smart makeup mirror device of claim 3, wherein the display mirror unit further comprises:
   a recognition sensor that operates on and off modes of the ring light based on a detection of the user; and
   a light adjustment module that operates a brightness adjustment mode of the ring light when a touch-and-drag gesture is input from one end to another end by the user.

5. The smart makeup mirror device of claim 3, wherein, when the support frame is rotated at a predetermined angle in a circumferential direction of the support frame, the display module is integrated with an artificial intelligence voice assistant by the voice signal of the user.

6. The smart makeup mirror device of claim 3, wherein the display mode comprises:
   an artificial intelligence voice assistant mode that provides life information based on a preset algorithm based on the voice signal or touch signal of the user;
   a skin diagnosis mode that diagnoses the skin condition of the user photographed by the camera; and
   an augmented reality makeup mode that provides information on a cosmetic product suitable for the skin condition of the user based on a skin diagnosis result obtained from the skin diagnosis mode.

7. The smart makeup mirror device of claim 3, wherein the support frame includes a plurality of heat dissipating holes for discharging a heat generated from the display mirror unit to an outside.

8. The smart makeup mirror device of claim 3, wherein the mood lamp is provided in a form of line-LED which circumferentially and continuously extends around a center of the rear surface of the support frame.

9. The smart makeup mirror device of claim 1, wherein the main body comprises:
   a tower housing including: a lower circumferential surface in which a plurality of speaker grill holes are formed in a lower circumferential surface of the tower housing; and
   an upper end to which the display mirror unit is rotatably mounted;
   a control switch disposed on a front surface of the tower housing; and
   a charging port disposed on a rear surface of the tower housing to supply power.

10. The smart makeup mirror device of claim 9, wherein the main body further comprises a suction cup pad for fixing to the floor surface, wherein the suction cup pad is made of an elastic material and disposed on a bottom surface of the tower housing.

11. The smart makeup mirror device of claim 9, wherein the control switch comprises:
   an artificial intelligence voice assistant switch for turning on and off an integration with the artificial intelligence voice assistant controlling an operation of the display mirror unit based on the voice signal;

a Bluetooth switch for turning on and off a Bluetooth function between a mobile phone of the user and the speaker; and a volume switch for adjusting a volume of the speaker.

12. The smart makeup mirror device of claim 11, wherein, when the artificial intelligence voice assistant switch is turned on and the display module rotates at a predetermined angle in the circumferential direction, the artificial intelligence voice assistant is implemented by the voice signal of the user.

13. The smart makeup mirror device of claim 6, wherein the artificial intelligence voice assistant mode is implemented when the display module is horizontally oriented, and the skin diagnosis mode or the augmented reality makeup mode is implemented when the display module is vertically oriented.

* * * * *